United States Patent [19]

Greene et al.

[11] Patent Number: 5,179,122

[45] Date of Patent: Jan. 12, 1993

[54] NUTRITIONAL SUPPLEMENT CONTAINING VITAMIN E

[75] Inventors: Carol J. Greene; Stephen H. W. Wu; Andreas M. Papas, all of Kingsport, Tenn.

[73] Assignee: Eastman Kodak Company, Rochester, N.Y.

[21] Appl. No.: 653,832

[22] Filed: Feb. 11, 1991

[51] Int. Cl.$^5$ ............... A61K 31/715; A61K 31/355; A61K 9/14; A61K 9/16
[52] U.S. Cl. .................... 514/458; 514/57; 514/937; 424/489; 424/496; 424/498
[58] Field of Search ............... 424/195.1, 489, 496, 424/498; 514/458, 937, 57

[56] References Cited

U.S. PATENT DOCUMENTS

| | | | |
|---|---|---|---|
| 2,978,446 | 4/1961 | Battista et al. | 260/212 |
| 3,253,992 | 5/1966 | Brooks | 167/81 |
| 4,201,235 | 5/1980 | Ciavatta | 132/7 |
| 4,231,802 | 11/1980 | McGinley et al. | 106/197 |
| 4,551,332 | 11/1985 | Stillman | 424/195.1 |
| 4,954,332 | 9/1990 | Bissett | 424/59 |

FOREIGN PATENT DOCUMENTS

| | | |
|---|---|---|
| 184942 | 6/1986 | European Pat. Off. . |
| 3224619 | 5/1983 | Fed. Rep. of Germany . |
| WO89/03689 | 5/1989 | PCT Int'l Appl. . |

OTHER PUBLICATIONS

M. G. Traber et al., *Am. J. Clin. Nutr.*, 44, (1986), pp. 914-923.
M. G. Traber et al., *Am. J. Clin. Nutr.*, 48, (1988), pp. 605-611.
N. Hidiroglou et al. *J. Animal Sci.*, (1988), pp. 3227-3234.
R. Patton, *Feedstuffs*, Apr. 24, 1989, p. 69.
H. E. Gallo-Torres, *Vitamin E, A Comprehensive Treatise*, vol. 1, L. J. Machlin, Ed., Marcel Dekker, Inc., New York (1980), pp. 181, 182.
T. Kimura et al., *Chem. Pharm. Bull.*, 37(2), Feb. 1989, pp. 439-441.
B. O. Roneus et al., *Equine Veterinary Journal*, 18(1), (1986), pp. 50-58.
K. M. Thakker et al., *Am. J. Clin. Nutr.*, 45, (1987), pp. 1472-1479.
N. E. Bateman et al., *J. Pharm. Pharmacol.*, 37, (1985), pp. 728-729.
N. E. Bateman et al., *J. Pharm. Pharmacol.*, 36, (1984), pp. 461-464.
L. Hatam et al., *Journal of Lipid Research*, vol. 20 (1979), pp. 639-645.

*Primary Examiner*—John W. Rollins
*Assistant Examiner*—Ralph Gitomer
*Attorney, Agent, or Firm*—Betty J. James; William P. Heath, Jr.

[57] ABSTRACT

A composition for increased bioavailability of Vitamin E. The composition contains a Vitamin E material, a surface active agent, an inert carrier, and, optionally, a flow agent.

7 Claims, No Drawings

NUTRITIONAL SUPPLEMENT CONTAINING VITAMIN E

FIELD OF INVENTION

The present invention concerns a composition containing Vitamin E, a surface active agent, and an inert carrier and a process for production thereof.

BACKGROUND OF THE INVENTION

Vitamin E is commonly found in vegetation and more abundantly in seeds from which tocopherols, in the natural state, are easily absorbed and utilized in humans and animals, wild and domestic. Processing of foods and feeds by industry for long term storage promotes accelerated degradation of Vitamin E content. To compensate for the loss of natural Vitamin E from food sources, nutritional supplements of natural or synthetic Vitamin E are administered by injection or orally. It is well known that tocopherols are unstable molecules. To improve tocopherol stability, manufacturing processes generally attach an acetate or succinate group to tocopherol, making Vitamin E acetate or succinate (d- or dl-alpha-tocopheryl acetate or succinate). These modifications may decrease the bioavailability of tocopherol and create a need for a more readily bioavailable Vitamin E. In some species both the alpha-tocopherol and alpha-tocopheryl acetate even in water dispersible forms are not bioavailable. Patton in "Feedstuffs", Apr. 24, 1989, p. 69, reported that in zoo animals dosed with dl-alpha-tocopheryl acetate, one-half of the administered tocopherol was absorbed, the remaining being excreted unchanged.

Enhanced absorption of Vitamin E acetate (VEA) has been studied previously by using aqueous dispersions and solubilized preparations. Several studies suggest that in the intestine, absorption of Vitamin E is influenced by presence of certain dietary lipids and the hydrophilic nature of the dosage form. Gallo-Torres (*In Vitamin E. A Comprehensive Treatise;* Machlin, L. J., Ed.; Marcel Dekker: New York, 1980; Vol. 1, p. 182) cited a report showing enhanced absorption of tocopherol by solubilizing tocopherol in medium-chain triglycerides. The work of Schnandke and Schmidt, described by Gallos-Torres (*In Vitamin E, A Comprehensive Treatise,* supra, p. 181) showed that a VEA in a 3% aqueous solution of Tween-80 was absorbed at twice the rate of a vegetable oil solution of VEA. In a study by Kimura et al. (*Chem. Pharm. Bull.,* 37(2), pp. 439–441) enhanced absorption of tocopherol in rats was promoted by an aqueous lecithin dispersed Vitamin E acetate containing medium chain triglycerides. While these reports showed that aqueous dispersions enhance Vitamin E absorption in some species, it has been discovered that elephants and black rhinoceros do not absorb some water dispersible forms well. These works also show that one cannot assume that water dispersible VEA of natural or synthetic origin will be readily bioavailable. However, these works have demonstrated that enhanced absorption of Vitamin E was promoted by solubilized Vitamin E and aqueous dispersions of Vitamin E.

It is well known that the efficacy of the hydrophilic nature of aqueous Vitamin E solutions and dispersions upon enteral absorption of Vitamin E can be demonstrated by increased absorption of hydrophilic Vitamin E by the normal and compromised intestine. It is known in the art that the source of Vitamin E, natural or synthetic, also affects its bioavailability. In the compromised gut, Vitamin E absorption was studied in patients with lipid malabsorption syndromes such as cholestatic liver, and cystic fibrosis. Such patients are unable to absorb Vitamin E or other dietary lipids. When a water soluble form of Vitamin E (d-alpha-tocopheryl polyethylene glycol 1000 succinate, or "TPGS") was administered orally to such patients, an elevation of blood tocopherol was detected within one week. When the same patients were dosed with tocopherol in vegetable oil, there was no significant increase of tocopherol in the blood, (Traber M. G., Thellman, C. A., Rindler, M. J., Herbert, J. K., *Am. J. Clin. Nutr.,* 1988, 48, 605–611). Thus, the type of tocopherol, natural or synthetic, and the hydrophilic nature of TPGS can be important in determining the absorption and bioavailability of Vitamin E in humans and animals.

A human clinical trial conducted by the National [Research Council of Canada and animal trials of Hidiroglou et al. (J. Animal Sci., 1988, 66:3227 3234) studied the relative bioavailability of natural and synthetic Vitamin E and both concluded that the natural Vitamin E has a bioavailability higher than previously thought.

The advantage of administering Vitamin E in a water-dispersible formulation was shown by Bateman et al. (*J. Pharm. Pharmacol.,* 1984, 37(7), 461–464) in a human clinical study in which Vitamins A, E, and $B_2$ were formulated into a liquid vehicle (Aqua Biosorb) and encapsulated into soft gelatin capsules which were given orally. In the formulation, $B_2$ was incorporated into the formulation as a suspension with a particle diameter of $\leq 100$ nm. The soft elastic gelatin capsules contained by weight % 20% polysorbate 80, 1% sorbitan monooleate and 79% distilled monoglyceride as the water dispersible base. Bateman demonstrated that the hydrophilic nature of water soluble Vitamin $B_2$, in addition to the lipid soluble Vitamins A and E in his dosage formulation, showed enhanced absorption.

Brooks describes in U.S. Pat. No. 3,253,992 the composition of anhydrous water dispersible fat soluble vitamin preparations and aqueous dispersions of these preparations. The Brooks patent requires only polyoxyethylene sorbitan monooleate and a distilled monoglyceride derived from safflower oil (Myverol 18–98) as the emulsifier and lipid soluble vitamins. The Brooks patent does not address the use of monoglyceride blends or the use of TPGS, a potent biologically active tocopherol, as an emulsifier. We have discovered that such aqueous dispersions have limited stability in vitro.

Stillman in U.S. Pat. No. 4,551,332 teaches the use of frozen solutions of Vitamin E blends comprised of glyceryl mono- and distearate and in some cases Jojoba oil for dermatological and cosmetic applications. Dispersibility in aqueous systems and oral use for humans and animals are not addressed.

With the exception of the Stillman patent, all other prior art cited above discussed lipid soluble nutrients which were administered as an aqueous dispersion. Other literature disclosed the use of TPGS as a solution. Heretofore, nothing exists in the prior art which teaches delivery of Vitamin E in a substantially anhydrous vehicle which is a free-flowing solid and readily dispersed in aqueous media in vivo to provide enhanced enteral bioabsorption.

SUMMARY OF THE INVENTION

In accordance with the invention, the composition for an aqueous dispersible, free-flowing solid with enhanced bioabsorption and easy handling is a lipid melt blend comprised of a lipid soluble melt blended Vitamin E as the active ingredient and surface active agents to correct the hydrophilic/lipophilic balance (HLB). Vitamin E blend and surface active agents both comprise the melt blend which is absorbed onto an inert carrier to absorb the melt blend. More specifically, the present invention is directed to a composition comprising (A) about 4 to about 59 weight % of a Vitamin E material having an HLB less than that of component (B), (B) about 1 to about 36 weight % Of at least one ionic, nonionic, or amphoteric surface active agent having an HLB of about 2 to about 20, and (C) about 40 to about 60 weight % of at least one inert carrier, wherein a blend of components (A) and (B) has an HLB of about 7 to about 14.

The above percentages are based on the weight of the three components such that the total amount of components (A) plus (B) plus (C) will be 100%.

A mixture of components (A) and (B) must form a suspension that will not visibly phase separate upon standing at room temperature for 24 hours.

A preferred composition of the invention can be described as a water dispersible, substantially anhydrous, free flowing solid composition comprising (A) about 4 to about 59 weight % of Vitamin E acetate, (B) about 1 to about 36 weight % of an alpha tocopherol polyethylene glycol ester, and (C) about 40 to about 60 weight % of an inert carrier, wherein said combination has a property of synergistic Vitamin E bioavailability, especially in horses.

The present invention is also directed to a process for preparing a composition comprising (A) about 4 to about 59 weight % of a Vitamin E material having an HLB less than that of component (B), (B) about 1 to about 36 weight % of at least one ionic, nonionic, or amphoteric surface active agent having an HLB of about 2 to about 20, and (C) about 40 to about 60 weight % of at least one inert carrier, wherein a blend of components (A) and (B) has an HLB of about 6 to about 14, said process comprising (i) melt blending components (A) and (B) until a substantially homogeneous melt phase is obtained, (ii) contacting said melt phase with component (C), (iii) cooling the blend made from step (ii) while agitating until the freezing point of the melt is achieved to result in a frozen blend.

DETAILED DESCRIPTION OF THE INVENTION

The present invention provides a Vitamin E nutritional supplement which is quickly and efficiently absorbed to optimal therapeutic tissue levels, is easily dispersed into an aqueous system, and is a free-flowing solid which is easy to handle. The combination of component (A) (i.e., the Vitamin E material) and component (B) (i.e., the surface active agent) substantially raises the melt temperature of the frozen blend. This physical characteristic of the blend allows the blend to be melted and blended to homogeneity and then absorbed onto an inert carrier and cooled to the freezing temperature of the Vitamin E blend thereby producing a free-flowing anhydrous solid which is water dispersible. This unexpected result is used to increase surface area of the blend by a composition that produces a free-flowing solid which is easy to handle and is easily dispersed in aqueous systems.

In the composition of the invention it is preferred that the amount of component (A) is about 24 to about 45 weight %; the amount of component (B) is about 15 to about 36 weight %; and the amount of component (C) is about 40 to about 60 weight %. The most preferred amount of component (C) is about 40 weight %.

In the composition of the invention it is also preferred that the HLB of component (A) is less than about 2, the HLB of component (B) is about 14 to about 18, and the HLB of a blend of components (A) and (B) is about 8 to about 10.

The composition of the invention optionally further comprises about 0.01 to about 25 weight %, based on the total weight of the composition, of at least one flow agent. Flow aids are compounds which improve flow properties by altering surface properties of the absorbed frozen blend by reducing tackiness and increasing slip, the ability of particles to slide over one another. Dispersibility, dissolution or bioavailability should not be compromised by the presence of flow aids. Examples of flow aids are silicone dioxide, talc and the like. Silicone dioxide is the most preferred flow aid because it can absorb oil several times its weight and it has a low bulk density.

The composition of the invention is preferably anhydrous. The Vitamin E material of component (A) can be any Vitamin E material having the required HLB value. The most preferred Vitamin E material for use as component (A) is Vitamin E acetate ("VEA"). Vitamin E succinate (VES) alone or in combination with VEA is also specifically contemplated for use as component (A). The HLB value of VEA is in the range of 1 to 4 and the HLB value of VES is in the range of 1 to 4.

The surface active agent for use as component (B) can be any edible surface active agent having the required HLB value. Such surface active agents may be water soluble or water dispersible, alone or combined, which modify the surface of the Vitamin E of component (A) to allow dispersion or solvation in aqueous media. The surface active agent or a blend thereof should be a HLB in the range of about 2 to about 20. In the case of surface active agents such as TPGS, an HLB value of about 14 to about 18 is preferred, in the case of surface active agents such as monoglyceride(s) an HLB value of about 4 to about 8 is preferred.

The surface active agents are surfactants which may be classified as nonionic, ionic and amphoteric. The nonionic surfactants may be further subdivided into classes such as polyethylene glycols, to which TPGS belongs, and the polyoxyethylenes such as Tweens, Aracels, Brijs, Myrjs, Spans and the like.

Ionic surfactants include anionic and cationic surfactants. Generally, the anionic surfactants are employed in preparations for internal consumption by both humans and animals. Examples of ionic surfactants include sodium and calcium salts of stearyl lactylate, phosphated mono- and diglycerides and the like.

Amphoteric surfactant may include phospholipids, phosphatidyl ethanolamines and the like.

Surfactants of low HLB, ionic and amphoteric may be combined with surfactants of high HLB to yield an HLB within the desired range to form stable dispersions of Vitamin E. A preferred blend of surfactants useful herein as component (B) is Myvatex Texture Lite food emulsifier which has a HLB in the range of 4 to 8.

Most preferably component (B) is d-alpha-tocopheryl polyethylene glycol ester, especially TPGS. This TPGS material is a waxy compound that is represented by the formula:

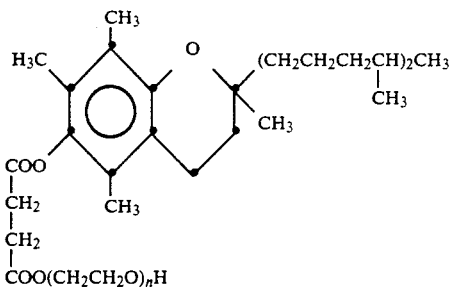

TPGS is prepared by the esterification of polyethylene glycol 1000 to the acid group of crystalline d alpha tocopheryl acid succinate. The HLB of TPGS is greater than 13.

In the preferred situation TPGS functions as the surface active agent and as a nutrient.

The inert carrier of component (C) can be any compatible and edible inert carrier. Inert carriers are compounds which function to increase the surface area of the frozen blend by absorbing the melt blend which freezes on the surface or within channels of the carrier. The carrier should not react with the Vitamin E/surfactant blend to alter chemical properties of the blend, and the carrier should easily release the blend to form a dispersion or solution in aqueous based systems. Examples of inert carriers are micro-crystalline cellulose, food starches, silicone dioxide, pharmaceutical clays, grain meals and cellulosic gums such as gum arabic. Cellulosic materials such as microcrystalline cellulose and similar celluloses are preferred carriers.

It is preferred the inert carrier has a particle size of about −120 mesh to about +400 mesh, U.S. standard sieve size, more preferred is about −5 mesh to about +325 mesh.

In the process of the invention the melt phase or blend is absorbed onto an inert carrier to provide a free-flowing solid dosage form which is readily dispersed in aqueous media, easy to handle, and enhances bioavailability of Vitamin E.

Preferred conditions for the process of the invention are wherein the temperature for steps (i) and (ii) is about 60° C. to about 90° C., and the melt phase is cooled in step (iii) to a temperature of about 45° C. to about 55° C.

Also, it is preferred that step (ii) is carried out under agitation and the amount of agitation for steps (ii) and (iii) is sufficient to substantially evenly distribute the melt phase on or into the carrier.

A preferred process of the invention can be described by the following steps: combining component (A) (i.e., Vitamin E material) and component (B) (i.e., the surface active agent) in a heated container such as Ross planetary mixer and heating to the melting point of the blend and thoroughly mixing until a single molten phase blend is obtained. As mixing and heating are continued, an inert carrier is added to the molten blend and stirred to make a homogeneous mixture, allowing the lipid soluble blend to absorb. Mixing is continued without heating until the freezing point of the lipid soluble blend is reached. Flow aids may be added to the blend before or after the nutrient blend has frozen. The best time to add flow aid is after the blend has solidified so that only the surface of the product is altered by the flow aid to increase slip or gliding character of the product. This will reduce the amount of flow aid needed in the process.

This invention is illustrated by the following examples but should not be interpreted as a limitation thereon.

EXAMPLES

EXAMPLE 1

This example illustrates the surface active nature of TPGS and Myvatex Texture Lite ® food emulsifier. The surface tension of TPGS was determined as a function of concentration in water at room temperature. The surface tension of Myvatex Texture Lite was measured as function of concentration.

Results show that the critical micelle concentration for TPGS solution is about 0.01 g/100 mL and Myvatex Texture Lite is about 0.01 g/100 mL (see FIG. 2). Myvatex Texture Lite was as surface active as TPGS; therefore Myvatex Texture Lite may promote enhanced bioabsorption of lipid soluble compounds because of its similar surface characteristics.

EXAMPLE 2

Example 2 illustrates the effect of TPGS upon the melt temperature of VEA/TPGS blends. A small amount of TPGS is used to increase the melt temperature of VEA above room temperature. Such mixtures yield blends which can freeze on carrier agents to make free flowing solids. In this example, miscibility of the blends was investigated by determining the melt temperature of various blend ratios. VEA and TPGS were weighed and combined as given in the table below to make 10 g of blend. The mixture was heated and blended to a homogeneous blend and cooled to room temperature. The melting point of each blend was determined by differential scanning calorimetry.

| VEA/TPGS (wt. %) | Melt Temperature (°C.) |
| --- | --- |
| 100/0 | 2.9 |
| 98/2 | 38.5 |
| 90/10 | 38.3 |
| 75/25 | 42.7 |
| 60/40 | 42.9 |
| 50/50 | 44.4 |
| 40/60 | 43.9 |
| 30/70 | 45.8 |
| 25/75 | 44.5 |
| 0/100 | 43.5 |

Although the 98/2 blend was a viscous liquid, the melt temperature was close to that of the other blends. At room temperature, 25% TGPS was required to solidify VEA. As usually observed in phase diagrams, a minimum melting temperature of the blend was not observed in this series of blends. The rise in temperature was sharp and remained constant over the range of concentrations.

EXAMPLE 3

This example illustrates the affect of Myvatex Texture Lite food emulsifier on the melt temperature of VEA. The solid blend was formulated as described in Example 2. Results for differential scanning calorimetry are given below.

| VEA/Myvatex Texture Lite (wt. %) | Melt Temperature (°C.) |
|---|---|
| 100/0 | 2.9 |
| 75/25 | 52.3 |
| 70/30 | 55.0 |
| 60/40 | 59.3 |
| 50/50 | 55.9 |
| 40/60 | 49.6 |
| 25/75 | 58.2 |
| 0/100 | 57.5 |

Results show that the combination of VEA with Myvatex Texture Lite at 25% or more alters the physical state of VEA from a liquid to a solid at room temperature.

EXAMPLE 4

This example illustrates the preparation of a free-flowing VEA/TPGS blend absorbed into an inert carrier to provide easy handling and enhanced bioavailability of VEA. This combination will be used in Example 5 to demonstrate enhanced bioavailability of VEA.

1. A 100 g sample of VEA, 1.360 international units (IU)g, and a 100 g sample of TPGS, 387 IUg, were weighed and combined in a temperature controlled mixer such as a Ross planetary mixer, and heated to 65° C. The sample was continuously stirred as the TPGS was melted. The molten state was blended to a single phase.

2. The warmed molten blend was mixed with 200 g of microcrystalline cellulose and mixing was continued until the blend was thoroughly absorbed. Mixing was continued without heating until the temperature of the molten blend had reached its freezing point.

The final product could be poured. This example shows the need for a flow aid. This product was easily dispersed into water and the cellulose readily settled. Analysis of the aqueous phase revealed that the Vitamin E content of the solid product was recovered in the aqueous phase.

TPGS has an hydrophilic lipophilic balance (HLB) in the range of 10-15. Both tocopheryl products are available from Eastman Chemical Products, Inc., Kingsport, Tennessee, U.S.A.

Microcrystalline cellulose is Avicel ® PHI101 and is available from FMC Corporation.

EXAMPLE 5

This example illustrates the enhanced bioavailability of the product described in Example 4, a blend of TPGS/Vitamin E acetate.

The sources of Vitamin E tested in this work were as follows:

1. Synthetic dl-alpha-tocopheryl acetate (solid water dispersible) from Rhone-Poulenc was used as the control.
2. Solid water dispersible d-alpha-tocopheryl acetate (Vitamin E acetate E 700), a Vitamin E acetate treated with gelatin which functions as a dispersing agent in an aqueous environment.
3. TPGS, the only water soluble form of tocopherol.
4. A blend of d alpha tocopheryl acetate (Vitamin E acetate E 6-100) with TPGS formulated as described in Example 4.

Products 2-4 were from Eastman Chemical Products, Inc. The tocopheryl esters were of natural origin.

Twenty horses (5 horses/Vitamin E form) were used for a comparative evaluation of different Vitamin E forms. Plasma tocopherol was analyzed to assess bioavailability. Baseline blood samples were withdrawn on two consecutive days. Each horse was dosed with 2.0 g equivalent tocopheryl acetate each day for 35 days. Plasma tocopherol was determined by a HPLC method described by Hatam and Kayden (J. Lipid Res., 1979, Vol. 20, p. 639-645). Baseline tocopherol values were subtracted from all test data. Results show that after 5 days, tocopherol blood levels for TPGS and Vitamin E 6-100 were more than 3 times higher than the blood level for synthetic Vitamin E. The absorption rate for natural water dispersible Vitamin E 700 was less than half that of TPGS/VEA. After 35 days, blood levels for synthetic tocopherol was essentially unchanged. Tocopherol blood levels for natural water dispersible Vitamin E 700, TPGS and TPGS/VEA were greater than 4 times that of synthetic tocopherol in blood. On an international unit basis the three natural tocopherol products tested contained 36% more international units than the synthetic tocopheryl acetate and therefore, natural tocopherols should provide a 36% higher blood level.

This study has shown that TPGS/Vitamin E acetate provides enhanced bioavailability of Vitamin E acetate. Moreover, in the TPGS/E 6-100 composition, the tocopherol content of Vitamin E acetate E6-100 was 3 times that of TPGS. Therefore, the high blood level of tocopherol was from enhanced absorption of Vitamin E acetate. Although in this study, serum tocopherol as a function of TPGS was not done, data strongly suggest enhanced absorption of VEA.

Roneus et al. (Equine Vet. J., 1986, 18(1), pp. 50-58) performed a study in which 0, 200, 600, 1800, and 5400 mg doses of dl a tocopherol acetate were administered daily to horses. Their work demonstrated that as the tocopherol dosage level was increased, serum tocopherol levels increased almost linearly.

EXAMPLE 6

This example illustrates the use of Myvatex Texture Lite as the surface active agent (instead of TPGS) as described in Example 4.

The processing steps were followed as described in Example 4.

This blend was dispersed in water to a white opaque dispersion in which the carrier was settled.

EXAMPLE 7

This example illustrates the use of a three-component blend consisting of VEA/VES/TPGS. The blend is prepared as described in Example 4. The weight ratio of the forms of Vitamin E may vary from 50-65/20-30-/5-20, VEA/VES/TPGS and the preferred ratio is 1/1/1.

EXAMPLE 8

This example illustrates the use of a three-component blend composed of VEA/TPGS/monoglycerides. The blend is processed as described in Example 4. In this example, weight ratio of the composition of the Vitamin E melt blend may vary from 50-95/1-25/1-25, VEA/TPGS/monoglycerides. The preferred composition contains 10% or less TPGS.

The invention has been described in detail with particular reference to preferred embodiments thereof, but it will be understood that variations and modifications can be effected within the spirit and scope of the invention.

We claim:

1. A water-dispersible, substantially anhydrous, free-flowing solid composition comprising
   (A) about 4 to about 59 weight % of Vitamin E acetate,
   (B) about 1 to about 36 weight % of an alpha-tocopherol polyethylene glycol ester, and
   (C) about 40 to about 60 weight % of an inert carrier, wherein said combination has a property of synergistic Vitamin E bioavailability.

2. The composition of claim 1 wherein component (B) is d-alpha-tocopherylpolyethylene glycol 1000 succinate.

3. The composition of claim 1 wherein the inert carrier has a particle size of about −120 mesh to about +400 mesh, U.S. standard sieve size.

4. The composition of claim 1 wherein the inert carrier has a particle size of about −5 mesh to about +325 mesh, U.S. standard sieve size.

5. The composition of claim 1 wherein the amount of component (A) is about 24 to about 45 weight %; the amount of component (B) is about 15 to about 36 weight %; and the amount of component (C) is about 40 to about 60 weight %.

6. The composition of claim 1 further comprising about 0.1 to about 25 weight %, based on the total weight of the composition, of at least one flow agent.

7. The composition of claim 6 wherein said flow agent is selected from the group consisting of silicone dioxide, talc, and a mixture thereof.

* * * * *